(12) United States Patent
Sterenborg et al.

(10) Patent No.: US 10,139,388 B2
(45) Date of Patent: Nov. 27, 2018

(54) METHOD TO DETERMINE THE ABSORPTION COEFFICIENT IN TURBID MEDIA

(75) Inventors: Henricus Josephus Cornelus Maria Sterenborg, Capelle aan den Ijssel (NL); Stephen Chad Kanick, Wheeling, WV (US); Arjen Amelink, Gouda (NL); Dominic James Robinson, Rotterdam (NL)

(73) Assignee: QUASPEC B.V., Zevenhuizen (NL)

( * ) Notice: Subject to any disclaimer, the term of this patent is extended or adjusted under 35 U.S.C. 154(b) by 577 days.

(21) Appl. No.: 14/006,643

(22) PCT Filed: Mar. 26, 2012

(86) PCT No.: PCT/NL2012/050188
§ 371 (c)(1),
(2), (4) Date: Dec. 30, 2013

(87) PCT Pub. No.: WO2012/128634
PCT Pub. Date: Sep. 27, 2012

(65) Prior Publication Data
US 2014/0107951 A1     Apr. 17, 2014

Related U.S. Application Data

(63) Continuation of application No. PCT/NL2011/050205, filed on Mar. 24, 2011.

(51) Int. Cl.
*G01N 21/49* (2006.01)
*G01N 33/26* (2006.01)
(Continued)

(52) U.S. Cl.
CPC ........... *G01N 33/26* (2013.01); *A61B 5/0075* (2013.01); *G01N 21/274* (2013.01);
(Continued)

(58) Field of Classification Search
CPC combination set(s) only.
See application file for complete search history.

(56) References Cited

U.S. PATENT DOCUMENTS

| 6,014,204 A | 1/2000 | Prahl et al. | |
|---|---|---|---|
| 6,850,656 B1 * | 2/2005 | Bevilacqua | G01N 21/49 356/12 |

(Continued)

OTHER PUBLICATIONS

Kanick et al., "Measurment of the reduced scattering coefficient of turbid media using single fiber reflectance spectroscopy: fiber diameter and phase function dependence", Biomedical Optics Express, vol. 2, No. 1, Jan. 1, 2011.*

(Continued)

*Primary Examiner* — Jennifer Simmons
(74) *Attorney, Agent, or Firm* — Kilpatrick Townsend & Stockton LLP

(57) ABSTRACT

The invention relates to a method to determine the wavelength dependent absorption coefficient of a turbid medium using overlapping illumination-detection areas comprising the steps of a) retrieving a calibration spectrum (CA) from a reference measurement using a reference sample; b) carrying out a measurement on an actual sample for determining the absolute reflection spectrum ($R_{abs}$) using a raw spectrum measured on the sample ($S_{medium}$) and the calibration spectrum ($C_A$); C) using the absolute reflection spectrum ($R_{abs}$) for determining the wavelength dependent absorption coefficient by minimizing the difference between the measured absolute reflection spectrum ($R_{abs}$) and a model function ($R_{abs}^{model}$). wherein the model function ($R_{abs}^{model}$) is modelled using a predetermined equation based on prior knowledge of the combination of a dependence of the effective photon path length ($L_{PF}$) on a scattering phase function (PF); a dependence of the absolute reflectance in the absence of absorption ($R_{abs}^0$) on scattering (Continued)

phase function (PF). The invention further relates to a system and a computer program product for determining the wavelength dependent absorption coefficient of a turbid medium.

19 Claims, 2 Drawing Sheets

(51) Int. Cl.
A61B 5/00 (2006.01)
G01N 21/47 (2006.01)
G01N 21/27 (2006.01)
A61B 5/02 (2006.01)

(52) U.S. Cl.
CPC ........... *G01N 21/474* (2013.01); *G01N 21/49* (2013.01); *A61B 5/02007* (2013.01); *A61B 2560/0233* (2013.01)

(56) References Cited

U.S. PATENT DOCUMENTS

| 7,420,656 | B1* | 9/2008 | Sandusky | G01C 3/08 356/5.09 |
|---|---|---|---|---|
| 2008/0004842 | A1 | 1/2008 | Amelink et al. | |
| 2008/0194929 | A1 | 8/2008 | Pesach et al. | |
| 2010/0042005 | A1* | 2/2010 | Bigio | G01N 21/59 600/476 |
| 2010/0261958 | A1* | 10/2010 | Webb | A61B 1/043 600/104 |

OTHER PUBLICATIONS

Kanick et al., "Integration of single-fiber reflectance spectroscopy into ultrasound-guided endoscopic lung cancer staging of mediastinal lymph nodes", Journal of Biomedical Optics, vol. 15(1), Jan./Feb. 2010.*

Kanick et al., "Integration of single-fiber reflectance spectroscopy into ultrasound-guided endoscopic lung cancer staging of mediastinal lymph nodes", Journal of Biomedical Optics 15(1), 017004, Jan. 15, 2010.*

Kanick et al., "Empirical model of the photon path length for a single fiber reflectance spectroscopy device", Optics Express, vol. 17, No. 2, Jan. 19, 2009.*

Kanick et al., "Monte Carlo analysis of single fiber reflectance spectroscopy: photon path lengthand sampling depth", Phys. Med. Biol. 54 6991, Nov. 4, 2009.*

Amelink, Arjen et al., "Measurement of the local optical properties of turbid media by differential path-length spectroscopy," *Applied Optics* (May 20, 2004), 43(15):3048-3054.

Doornbos, R. M. P. et al., "The determination of in vivo human tissue optical properties and absolute chromophore concentrations using spatially resolved steady-state diffuse reflectance spectroscopy," *Phys. Med. Biol.* (1999), 44:967-981.

Kanick, Stephen C. et al., "Empirical model description of photon path length for differential path length spectroscopy: combined effect of scattering and absorption," *Journal of Biomedical Optics* (Nov./Dec. 2008), 13(6):064042-1-064042-8.

Kanick, S. C. et al., "Empirical model of the photon path length for a single fiber reflectance spectroscopy device," *Optics Express* (Jan. 19, 2009), 17(2):860-871.

Kanick, S. C. et al., "Monte Carlo analysis of single fiber reflectance spectroscopy: photon path length and sampling depth," *Phys. Med. Biol.* (2009), 54:6991-7008.

Phillips, et al., "Calculation of Photon Path Changes due to Scatter in Monte Carlo Simulations," $32^{nd}$ *Annual International Conference of the IEEE EMBS*, Buenos Aires, Argentina, Aug. 31-Sep. 4, 2010, pp. 4959-4962.

* cited by examiner

METHOD TO DETERMINE THE ABSORPTION COEFFICIENT IN TURBID MEDIA

FIELD OF THE INVENTION

The invention relates to a method for determining the absorption coefficient of turbid media.

The invention further relates to a system for determining the absorption coefficient of turbid media.

The invention still further relates to a computer program product comprising instructions for causing a processor to determine the absorption coefficient of turbid media.

BACKGROUND OF THE INVENTION

Non invasive measurement of the concentrations of different absorbing substances in optically turbid media, such as living tissue, is challenging. A commonly used method for this employs the measurement of the reflected light from such an optically turbid medium. An essential part of the light reflected from a turbid medium has travelled through the medium and was directed out of the medium by scattering. The main problem of such measurements is that the optical path length of the detected photons is strongly dependent on the optical properties, such as the absorption coefficient, the scattering coefficient and the angular distribution of scattering, also referred to as scattering phase function. As a result, the path length of detected photons is dependent on the measurement geometry and optical properties, and varies with wavelength. Absolute measurements of concentrations based on absorption spectroscopy in turbid media may be compromised by the dependence of the path length on the properties of a medium under consideration.

Classical reflectance spectroscopy devices known from the prior art often utilized multiple optical fibers to deliver and collect light during measurement. However, the potential advantages of reflectance probes with a single optical fiber to deliver/collect light are numerous. Advantages of the single fiber design include small probe size and simple device design, making it more-suitable than multi-fiber probes for clinical applications, such as optical biopsy of potential malignancies via endoscopy or biopsy needles. However, there exists no empirical or analytical description of light transport in the regime associated with overlapping source-detector areas, such as when using a single fiber.

An embodiment of a reflectance spectroscopy system using overlapping illumination-detection areas for determining the absorption coefficient in a turbid medium is known from Kanick et al. Phys. Biol. 54, 6991-7008 (2009). In the known embodiment a method is disclosed wherein a single fiber is used and positioned at a surface of the tissue under investigation. The fiber is used for illuminating the tissue as well as for collecting the reflected light.

It is a disadvantage of the known method that the dependence of the effective path length of photons on scattering phase function as well as the reduced scattering coefficients were guessed, which might lead to inaccurate determination of the absorption coefficient.

BRIEF DESCRIPTION OF THE INVENTION

It is an object of the invention to provide a method for determining the absorption coefficient of a turbid medium without knowledge of the scattering coefficient and scattering phase function when overlapping illumination and detection areas are used.

To this end the method according to the invention comprises the steps of:

retrieving a calibration spectrum ($C_\lambda$) from a reference measurement using a reference sample;

carrying out a measurement on an actual sample for determining the absolute reflection spectrum ($R_{abs}$) using a raw spectrum measured on the sample ($S_{medium}$) and the calibration spectrum ($C_\lambda$);

using the absolute reflection spectrum ($R_{abs}$) for determining the wavelength dependent absorption coefficient by minimizing the difference between the measured absolute reflection spectrum ($R_{abs}$) and a model function ($R_{abs}^{model}$), wherein the model function ($R_{abs}^{model}$) is being modelled using a pre-determined equation based on prior knowledge of the combination of i. a dependence of the effective photon path length ($L_{PF}$) on scattering phase function (PF);

ii. a dependence of the absolute reflectance in the absence of absorption ($R_{abs}^0$) on scattering phase function (PF).

It will be appreciated that a plurality of different per se known embodiments may be used for providing such overlapping illumination-detection geometry. In a preferred embodiment a single optical fiber is used, for example having dimensions between 10 μm and 3 mm.

In accordance with the invention a calibrated assessment of reflectance in the absence of absorption is used to appropriately estimate the combined effect that the reduced scattering coefficient and the scattering phase function have on the effective photon path length. Thereby estimation of the absorption coefficient is substantially improved.

Application of this methodology to measurement of living tissue provides aspects of vascular physiology which may be useful in characterization of tissue health status. For example, blood volume fraction, average vessel diameter and haemoglobin oxygen saturation, as well as concentrations of other light absorbing substances, including billirubin, beta-carotene, melanin, glucose, fat and water may be determined. In addition, the method can be used to measure concentrations of exogenous substances in tissue, such as drugs, optical contrast agents, dyes, pollutants, as long as hey have appropriate absorption properties in the wavelength region used.

The invention is based on the following insights. White-light reflectance measurements provide information about absorption and scattering properties of an optically sampled turbid medium such as tissue. Specifically the absorption coefficient $\mu_a$ relates to aspects of the tissue physiology. It is found that quantitative estimation of $\mu_a$ from a reflectance spectrum requires mathematical correction for the effects that $\mu_a$, reduced scattering coefficient $\mu_s'$ and scattering phase function PF have on the effective photon path length $L_{SF}$. An example of a mathematical representation of this relationship is given by equation (1):

$$\frac{L_{SF}^{model}}{d_{fiber}} = \frac{C_{PF} p_1}{(\mu_s' d_{fiber})^{p_2} + (p_3 + (\mu_a d_{fiber})^{p_3})} \quad (1)$$

wherein $C_{PF}$ describes the dependence of $L_{SF}$ on PF;

$d_{fiber}$ is a diameter of the fiber which is used for measurements.

It will be appreciated that the values 1.54, 0.18 and 0.64 correspond to the empirically established constants p1, p2, p3, respectively. These coefficients were established for the single fiber embodiment as reported in Phys. Biol. 54, 6991-7008 (2009), and may have different values for different conditions and or embodiments.

In the methods known from the prior art, practical application of equation (1) to analyze spectra measured in tissue in vivo has required an assumption about the tissue PF to estimate $C_{PF}$, as well as an assumption about the value of $\mu_s'$ at least at one wavelength. This approach is found to be not accurate.

It is further found that the single fiber reflectance intensity in the absence of absorption $R_{abs}^0$ showed a PF-specific dependence on dimensionless scattering, defined as the product of $\mu_s'$ and fiber diameter $d_{fiber}$. However, it will be appreciated that this finding may be generalized to any overlapping illumination-detection geometry. An example of a mathematical representation of the relation between $R_{abs}^0$ and dimensionless scattering is given in equation (2):

$$R_{abs}^0 = \eta_c \left(1 + P_4 e^{(-P_5 \mu_s' d_{fiber})}\right) \left[\frac{(\mu_s' d_{fiber})^{P_6}}{P_5 + (\mu_s' d_{fiber})^{P_6}}\right] \quad (2)$$

wherein, $\eta_c$ is the asymptotic value, i.e. the diffuse limit to the single fiber collection efficiency, which is proportional to the NA of the fiber and is about 2.7% for a single fiber with NA=0.22. $P_4$, $P_5$, $P_6$ are PF-specific parameters. It is found that for the single fiber embodiment, in equation (2) $P_5$ usually falls within the range of 4.3-9.2; $P_6$ usually falls within the range of 0.81-1.14 and $P_4$ usually falls in the range of 1.07-2.16. It will be appreciated that, although, not specified in equations (1) and (2) explicitly, $C_{PF}$, $\mu_s'$, $R_{abs}$ are variables which depend on the scattering phase function (PF). Therefore, the effective photon path length ($L_{PF}$) and the absolute reflectance in the absence of absorption ($R_{abs}^0$) are dependent on the scattering phase function (PF). In accordance with an aspect of the invention, the model function ($R_{abs}^{model}$) is modeled using inter alia a prior knowledge on the dependence of $L_{PF}$ and $R_{abs}^0$ on the scattering phase function (PF).

Accordingly, in accordance with the insight of the invention, first a reference calibration measurement is carried out. A sample having high scattering coefficient (such that $\mu_s' d_{fiber} > 10$) can be selected, because for very high scattering coefficients the collected reflectance becomes independent of the (often unknown) phase function of the calibration sample and approaches the diffuse limit $\eta_c$. Alternatively, a sample with a smaller scattering coefficient may be used if its phase function is known. The measurement may be performed with the fiber in contact with the calibration sample. However, other calibration geometries may be used. The absolute device calibration spectrum in case a high scattering reference sample is used can be calculated from the calibration measurement as follows:

$$C(\lambda) = \frac{\eta_c(NA(\lambda))}{S_{reference}(\lambda)} \quad (3)$$

wherein $C(\lambda)$ stands for the calibration spectrum of the measurement device using the calibration sample;

$S_{reference}(\lambda)$ stands for the raw, unprocessed spectrum measured on the calibration sample, $\eta_c(NA(\lambda))$ stands for the maximum reflection of a scattering sample. It is further found that $\eta_c(NA(\lambda))$ may depend slightly on the wavelength if the scattering coefficient of the calibration sample is wavelength dependent.

When the results of the calibration measurements are processed they are further used in the method of the invention in the following way.

The absolute reflection spectrum of a sample under investigation (tissue) may be obtained using the calibration data as follows:

$$R_{abs}(\lambda) = C(\lambda) S_{medium}(\lambda) \quad (4)$$

wherein $R_{abs}(\lambda)$ stands for the absolute reflection of the medium $S_{medium}(\lambda)$ stands for the raw, unprocessed spectrum of the actual sample (tissue).

At the next step in accordance with the invention, the optical properties are extracted from the measured spectrum $R_{abs}(\lambda)$. It is appreciated that a general problem in analysing such spectra is that three unknown parameters (reduced scattering coefficient $\mu_s'$, scattering phase function PF and absorption coefficient $\mu_a$) for each measurement point have to be calculated. As a result, the equations do not converge to a single solution.

In accordance with the invention the wavelength dependent absorption coefficient $\mu_a(\lambda)$ is calculated from the measured reflectance $R_{abs}(\lambda)$ by minimizing the difference between the measured absolute reflection spectrum $R_{abs}(\lambda)$ and the model function $R_{abs}^{model}(\lambda)$, wherein the model function $R_{abs}^{model}(\lambda)$ is modelled using a pre-determined equation based on prior knowledge of the combination of the dependence of the effective photon path length $L_{SFmodel}(\lambda)$ on the phase function PF (e.g. equation 1) and the dependence of the absolute reflectance in the absence of absorption $R_{abs}^0(\lambda)$ on the phase function PF (e.g. equation 2). The $R_{abs}^{model}(\lambda)$ may be modelled using the Lambert-Beer equation, according to $R_{abs}^{model}(\lambda) = R_{abs}^0(\lambda) e^{(-\mu_a(\lambda) L_{SFmodel}(\lambda))}$.

Accordingly, in accordance with the invention, in Equation (2) $\mu_s'$ is estimated from $R_{abs}^{model}$ such that the effect of a potential mis-estimation of $\mu_s'$ in Equation (1) is compensated by a corresponding mis-estimation of $C_{PF}$. In this way the effective path-length is close to its true value (within 7.5% for biological tissues), even when $C_{PF}$ and $\mu_s'$ are incorrectly specified. Preferably, the values for $C_{PF}$, $P_4$, $P_5$ and $P_6$ are chosen to be 0.944, 1.55, 6.82, and 0.969, respectively; this choice of parameters minimizes the error in estimated path length $L_{SFmodel}(\lambda)$.

It will be appreciated, however, that the compensative effect occurs for other combined values of $C_{PF}$, $P_4$, $P_5$ and $P_6$ as well. Furthermore, different mathematical expressions than shown in Eqs. (1) and (2) may also be used to describe the combined effect of phase function on photon path length $L_{SFmodel}(\lambda)$ and on absolute reflectance $R_{abs}^0(\lambda)$. Moreover, lookup tables that directly link $R_{abs}^0(\lambda)$ to a combined $C_{PF}$-$\mu_s'$ set can be used as well. This named compensative effect in the mis-estimation of the core parameters in the equations is found to be surprising, however enabling to solve a single equation having three unknowns. More details on the named compensative effect will be given with reference to FIG. 2.

In an embodiment of the method according to the invention the method further comprises the step of using a single fiber for delivering the light beam towards the sample and for collecting the reflected beam from the sample.

It is found that such solution may be practical for clinical purposes as both the impinging and the reflected beams may be delivered by the same fiber, allowing for small fiber-probe profiles and facilitating measurements through thin needles such as Fine Needle Aspiration needles.

In a further embodiment of the method according to the invention the light used for the calibration and sample measurements is generated by a plurality of monochromatic sources. However, it will be appreciated that a source having a continuous spectrum of wavelengths may also be used.

The system according to the invention for determining the wavelength dependent absorption coefficient of a diffuse medium for a light beam comprises:
  a light source adapted to generate the light beam;
  a processor adapted for:
    a. retrieving a calibration spectrum ($C_\lambda$) from a reference measurement using a reference sample;
    b. retrieving results of a further measurement on an actual sample for determining the absolute reflection spectrum ($R_{abs}$) using a raw spectrum measured on the sample ($S_{medium}$) and the calibration spectrum ($C_\lambda$);
    c. using the absolute reflection spectrum ($R_{abs}$) for determining the wavelength dependent absorption coefficient by minimizing the difference between the measured absolute reflection spectrum ($R_{abs}$) and a model function ($R_{abs}^{model}$),
       wherein the model function ($R_{abs}^{model}$) is modelled using a pre-determined equation based on prior knowledge of the combination of:
         i. a dependence of the effective photon path length ($L_{SF}$) on scattering phase function (PF);
         ii. a dependence of the absolute reflectance in the absence of absorption ($R_{abs}^0$) on scattering phase function (PF).

Advantageous embodiments of the system according to the invention are given in the dependent claims.

The computer program according to the invention comprises instructions for causing a processor to carry out the following steps:
  a. retrieving a calibration spectrum ($C_\lambda$) from a reference measurement using a reference sample;
  b. retrieving data of a measurement on an actual sample for determining the absolute reflection spectrum ($R_{abs}$) using a raw spectrum measured on the sample ($S_{medium}$) and the calibration spectrum ($C_\lambda$);
  c. using the absolute reflection spectrum ($R_{abs}$) for determining the wavelength dependent absorption coefficient by minimizing the difference between the measured absolute reflection spectrum ($R_{abs}$) and a model function ($R_{abs}^{model}$), wherein
  d. the model function ($R_{abs}^{model}$) is modelled using a pre-determined equation based on prior knowledge of the combination of
     i. a dependence of the effective photon path length ($L_{SF}$) on scattering phase function (PF);
     ii. a dependence of the absolute reflectance in the absence of absorption ($R_{abs}^0$) on scattering phase function (PF).

These and other aspects of the invention will be discussed in more detail with reference to figures wherein like reference numerals refer to like elements. It will be appreciated that the figures are presented for illustrative purposes and may not be used for limiting the scope of the appended claims.

DETAILED DESCRIPTION

Figure 1:
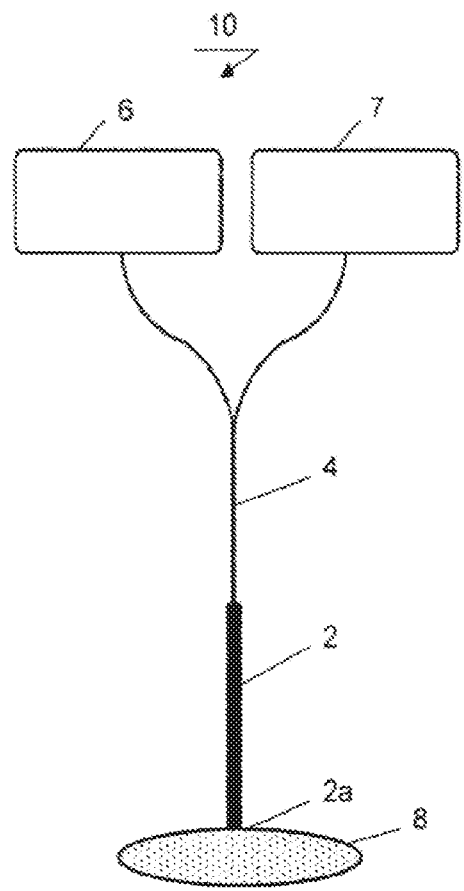
FIG. 1 presents in a schematic way an embodiment of a system which may be used for carrying out a calibration measurement.

FIG. 1 presents in a schematic way an embodiment of a system which may be used for carrying out a calibration measurement on a sample 8. For this purpose the system 10 comprises a probe 2, a bifurcated optical cable 4, one end of which is connected to a light source 6 and the other end of which is connected to a suitable spectrometer 7. Accordingly, the optical fiber 2 is used for delivering a light beam from the light source 6 to the sample and for collecting reflected light from the sample 8.

It is further found to be advantageous to polish the probe 2 at an angle larger than $\arcsin(NA/n_{sample})$ with respect to a vertical line for minimizing specular reflections, where NA is the numerical aperture of the fiber and $n_{medium}$ is the refractive index of the sample.

The reflectance of the sample is in case of a high scattering sample given by $R_{sample} = \eta_c(NA(\lambda))$.

When the absorption coefficient of a turbid medium (tissue) is to be determined, the equation 1 has to be used in a Lambert-Beer equation, according to $R_{abs} = R_{abs}^0 \exp(-\Box_a L_{SFmodel})$. In a general way, the equation 1 can be written as:

$$L_{SF\ model} = \frac{C_{PF} p_1 d_{fiber}}{(\mu_s' d_{fiber})^{p2}(p_3 + (\mu_a d_{fiber})^{p3})} \quad (5)$$

As has been indicated earlier, in equation (5) PF and $\mu_s'$ of tissue are not known, which implies that $C_{PF}$ is not known and that specification of $\mu_s'$ from reflectance $R_{abs}^0$ also requires knowledge of PF for specifying the correct constants $P_4$, $P_5$, and $P_6$ in equation 2.

In accordance with the invention, $\mu_s'$ is estimated from reflectance $R_{abs}^0$ such that a potential mis-estimation of $\mu_s'$ is compensated by a corresponding mis-estimation of $C_{PF}$.

It is found that the ratio of $C_{PF}/(\mu_s')^{p2}$ is approximately equal to its true value (within 7.5% for biological tissues), provided the $C_{PF}$ is properly linked to the phase function used to estimate $\mu_s'$ from $R_{abs}^0$ (i.e. $C_{PF}$ is linked to the values of $P_4$, $P_5$, and $P_6$ in equation 2).

It is found that as high angle scattering events become more likely, $R_{abs}^0$ increases because incident photons are more likely to be collected and the photon path length $L_{SF}$ decreases as those collected photons are likely to travel a shorter path.

Figure 2:
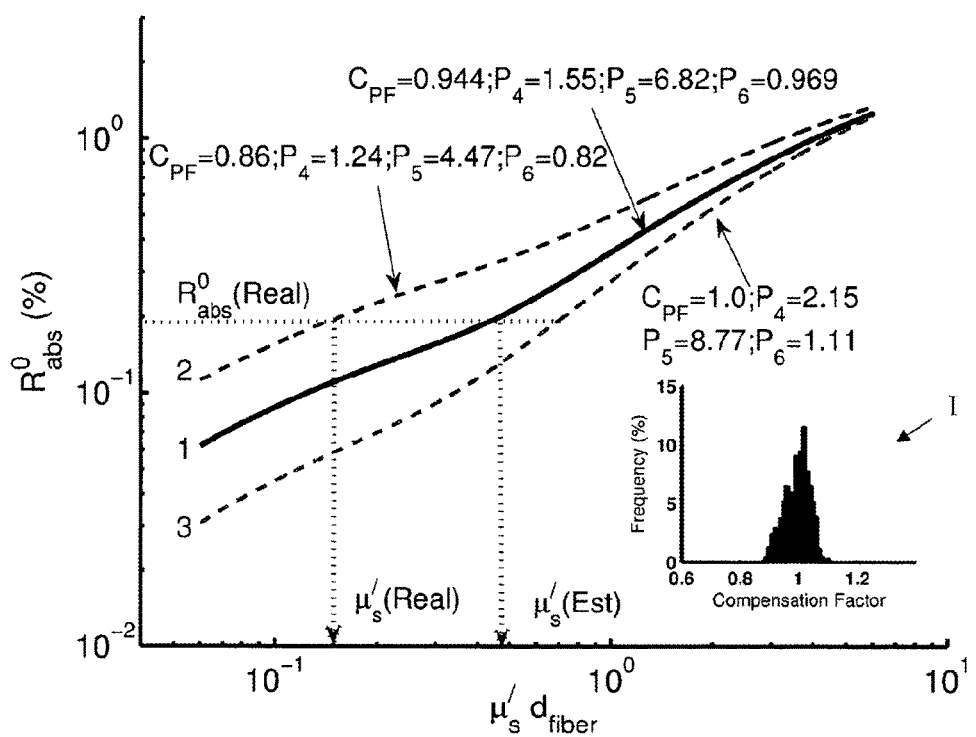
FIG. 2 presents a number of characteristic curves.

In FIG. 2, a number of characteristic curves is presented, wherein it is found that the curve for $C_{PF}=0.944$, $P_4=1.55$, $P_5=6.82$ and $P_6=0.969$ is an optimal curve for practicing the invention. FIG. 2 shows the relation between $R_{abs}^0$ and $\mu_s' d_{fiber}$ for 3 exemplary embodiments of known samples having different known phase functions PF with different backscattering components. The $C_{PF}$ values and $P_4$, $P_5$, and $P_6$ values for these phase functions PF are also indicated for each of these selected PF's. The graphs presented in FIG. 2 are calculated using equation (2) discussed with reference to the foregoing.

For an unknown sample, such as tissue, utilization of equations (1) and (2) to calculate the photon path length $L_{SF}$ requires an assumption about the phase function PF, which is also unknown.

It is found that it is particularly suitable to assume that the phase function PF is characterized by $C_{PF}=0.944$, $P_4=1.55$, $P_5=6.82$ and $P_6=0.969$ (see solid line, curve 1 in FIG. 2). However, it is also possible to implement the equation using the other curves given in FIG. 2, or any other alternative curves which may be produced using equation 2 or using Monte Carlo simulations applied to a known sample. However, it is found advantageous to select a curve whose reflectance properties are close to the reflectance properties which may be expected from a sample under investigation, such as tissue.

Utilization of the $P_4$, $P_5$ and $P_6$, discussed with reference to the foregoing regarding an assumed phase function PF in equation (2) corresponding to curve number 1 in FIG. 2, would yield an estimated value of $\mu_s'$ (Est) for an unknown sample based on a measured reflectance $R_{abs}^0$(Real).

The following effect has been found when analyzing equations (1), (2) and the graphs given in FIG. 2. Should the true sample phase function PF of an unknown sample be characterized by a higher backscattering component than the assumed PF (e.g. the true combination of parameters corresponding to true curve 2 in FIG. 2 is $C_{PF}$=0.86, $P_4$=1.24, $P_5$=4.47 and $P_6$=0.82), then the $\mu_s'$ would be overestimated from $R_{abs}^0$(Real) since $\mu_s'$ (Est)>$\mu_s'$(Real), see corresponding notations in FIG. 2.

However, the initially assumed $C_{PF}$ (0.944), corresponding to the assumed sample curve 1 is larger than the "true" $C_{PF}$ (0.86), corresponding to the "true" sample curve 2. Accordingly, an over-estimation of $C_{PF}$ compensates for the effect of over-estimation of $\mu_s'$ on $L_{SF}$ in Eq. (1).

Next, if the true phase function PF has in fact a smaller backscattering component than the value assumed for the phase function PF (e.g. the true sample PF corresponds to curve 3 in FIG. 2, instead of the assumed curve 2), then the resulting $\mu_s'$ (Est) obtained by using the assumed $R_{abs}^0$ curve 2 of FIG. 2 would be underestimated. Accordingly, also for this situation an effect of compensation takes place—i.e. an under-estimation of $C_{PF}$ in Eq. (1), since in this case the assumed $C_{PF}$ (0.944) was smaller than the "true" $C_{PF}$ (1.0).

Preferably, for the assumed scattering phase function $PF^{assumed}$ a gamma value between $\gamma$=1.6 and 1.8 is used, where gamma is related to the first and second moments ($g_1$ and $g_2$, respectively) of the scattering phase function according to $\gamma=(1-g_2)/(1-g_1)$.

The inter-related, compensating effects of mis-estimation of $C_{PF}$ and $\mu_s'$ through assumption of an estimated phase function PF can be further analysed by evaluation of the ratios $C_{PF}^{est}/C_{PF}^{real}$ and $(\mu_s'(Est)/\mu_s'(Real))^{0.18}$.

It is found that these two metrics either both are smaller than unity or both are greater than unity, indicating a compensating effect on estimates of $L_{SF}$. Moreover, the magnitudes of these effects are also very similar: $C_{PF}^{est}/C_{PF}^{real}$ ranges from 0.9 to 1.12 in biological tissues, while $(\mu_s'(Est)/\mu_s'(Real))^{0.18}$ ranges from 0.85 to 1.25 in case equation (2) is used to calculate $\mu_s'(Est)$ from $R_{abs}^0$.

The inset (I) in FIG. 2 shows a histogram plot of the ratio of these 2 metrics (defined as the compensation factor). It will be appreciated that perfect compensation of the effect of mis-estimation of $C_{PF}$ and $\mu_s'$ on path length would yield a compensation factor of 1.0. The histogram clearly shows a narrow distribution centred around 1.0, with 76% of the data within 5% of this value, and 99% of the data within 10% of this value.

It will be appreciated that while specific embodiments of the invention have been described above, the invention may be practiced otherwise than as described. For example, for specific turbid media different constants in the equations may be used. However, the method for determining the appropriate constants will lie within the ordinary skill of the person skilled in the art, when reducing the invention into practice.

The invention claimed is:

1. A method to determine the wavelength dependent absorption coefficient of an actual sample of a turbid medium without prior knowledge of an actual scattering coefficient using overlapping illumination and detection areas, wherein measurements are carried out using a single optical fiber for delivering a light beam towards the actual sample for illumination and for collecting a reflected light beam from the actual sample for detection, wherein a light spot of the delivered light beam used for illumination overlaps a light spot of the reflected light beam used for detection, the method comprising the steps of:
   a. retrieving a calibration spectrum from a reference measurement using a reference sample;
   b. measuring the actual sample using the single optical fiber to deliver a light beam towards the actual sample to determine an absolute reflection spectrum using a raw spectrum measured on the actual sample and the calibration spectrum;
   c. using the absolute reflection spectrum to determine the wavelength dependent absorption coefficient by minimizing the difference between the measured absolute reflection spectrum and a model function, wherein
   d. the model function is modelled using a pre-determined equation based on prior knowledge of the combination of:
      i. a dependence of an effective photon path length on a scattering phase function;
      ii. a dependence of the absolute reflectance in the absence of absorption on the scattering phase function; and
      iii. an assumed estimate for the scattering coefficient, wherein the effective photon path length and the absolute reflectance in the absence of absorption and are both a function of the assumed estimate for the scattering coefficient, wherein an influence of a mis-estimation of the scattering coefficient on the value of the absolute reflectance in the absence of absorption is at least partially compensated by the influence of the mis-estimation of the scattering coefficient on the value of the effective photon path length such that the wavelength dependent absorption coefficient of the actual sample of the turbid medium is determined without prior knowledge of the actual scattering coefficient of the actual sample.

2. The method according to claim 1, wherein the calibration spectrum is retrieved by a measurement performed with the single fiber in contact with the calibration sample for retrieving an absolute device calibration spectrum.

3. The method according to claim 2, where for the calibration measurement a scattering reference sample is used having a scattering coefficient such that $\mu_s' \, d_{fiber}$>10, wherein $\mu_s'$ is the calibration sample's reduced scattering coefficient and $d_{fiber}$ is the single fiber's diameter.

4. The method according to claim 1, wherein light used for the measurements is monochromatic or continuous spectrum light.

5. The method according to claim 1, wherein light used for measurements comprises a continuous spectrum of wavelengths.

6. The method according to claim 1, wherein the turbid medium is tissue.

7. The method according to claim 1, wherein the absorption coefficient is related to the concentration and/or packaging of absorbing molecules selected from the group consisting of hemoglobin, bilirubin, beta-carotene, melanin, cytochrome, glucose, lipid and water.

8. The method according to claim 1, wherein for the assumed scattering phase function a gamma value between $\gamma$=1.6 and $\gamma$=1.8 is used, where gamma is related to the first and second moments, g1 and g2, respectively, of the scattering phase function according to $\gamma=(1-g2)/(1-g1)$.

9. The method according to claim 1, where for the calibration measurement a reference sample of known phase function and scattering coefficient is used.

10. The method according to claim 1, wherein the model function is described by the following equation:

$R_{abs}^{model}=R_{abs}^0 \cdot \exp(-\mu_a \cdot L_{SF}^{model})$; wherein $R_{abs}^{model}$ is the model function;
$\mu_a$ is the wavelength dependent absorption coefficient;
$R_{abs}^0$ is the absolute reflectance in the absence of absorption; and
$L_{SF}^{model}$ is the effective photon path length.

11. The method according to claim 1, wherein the absolute reflectance in the absence of absorption is described by the following equation:

$$R_{abs}^0 = \eta_c \left(1 + P_4 e^{(-P_5 \mu_s' d_{fiber})}\right) \left[\frac{(\mu_s' d_{fiber})^{P_6}}{P_5 + (\mu_s' d_{fiber})^{P_6}}\right],$$

wherein
$R_{abs}^0$ is the absolute reflectance in the absence of absorption;
$\mu_s'$ is the assumed estimate for the scattering coefficient;
$\eta_c$ is an asymptotic value at a diffuse limit to a single fiber collection efficiency;
$d_{fiber}$ is a diameter of a fiber which is used for measurements; and
$P_4$, $P_5$, $P_6$ are scattering phase function (PF) specific parameters.

12. The method according to claim 1, wherein the effective photon path length is described by the following equation:

$$L_{SFmodel} = \frac{C_{PF} p_1 d_{fiber}}{(\mu_s' d_{fiber})^{p_2}(p_3 + (\mu_a d_{fiber})^{p_3})},$$

wherein
$L_{SF}^{model}$ is the effective photon path length;
$\mu_s'$ is the assumed estimate for the scattering coefficient;
$d_{fiber}$ is a diameter of a fiber which is used for measurements;
$C_{PF}$ describes dependence of the effective photon path length on the scattering phase function; and
$P_1$, $P_2$, $P_3$ are empirically established constants.

13. A system for determining the wavelength dependent absorption coefficient of an actual sample of a turbid medium without prior knowledge of an scattering coefficient using overlapping illumination and detection areas comprising:
1) a light source adapted to generate a light beam for illumination of the actual sample;
2) a spectrometer for detecting a reflected light beam from the actual sample and carrying out spectrum analysis based on measurement data;
3) a bifurcated optical cable, a first end of which is connected to the light source, a second end of which is connected to the spectrometer, the first and second ends being connected to a probe formed by a single optical fiber for delivering the light beam from the light source towards the actual sample for illumination and for collecting the reflected light beam from the sample for detection, wherein a light spot of the delivered light beam used for illumination overlaps a light spot of the reflected light beam used for detection; and
4) a processor adapted for:
   a. retrieving a calibration spectrum from a reference measurement using a reference sample;
   b. retrieving results of a further measurement on the actual sample using the single optical fiber to deliver a light towards the actual sample to determine the absolute reflection spectrum using a raw spectrum measured on the actual sample and the calibration spectrum;
   c. using the absolute reflection spectrum for determining the wavelength dependent absorption coefficient by minimizing the difference between the measured absolute reflection spectrum and a model function, wherein for the model function is modelled using a pre-determined equation based on prior knowledge of the combination of:
      i. a dependence of the effective photon path length on a scattering phase function;
      ii. a dependence of the absolute reflectance in the absence of absorption on the scattering phase function; and
      iii. an assumed estimate for the scattering coefficient, wherein the effective photon path length and the absolute reflectance in the absence of absorption and are both a function of the assumed estimate for the scattering coefficient, wherein an influence of a mis-estimation of the scattering coefficient on the value of the absolute reflectance in the absence of absorption is at least partially compensated by the influence of the mis-estimation of the scattering coefficient on the value of the effective photon path length such that the wavelength dependent absorption coefficient of the actual sample of the turbid medium is determined without prior knowledge of the actual scattering coefficient of the actual sample.

14. The system according to claim 13, wherein the light source comprises a monochromatic or continuous spectrum light source.

15. The system according to claim 13, wherein the single fiber is provided in an interventional instrument.

16. The system according to claim 15, wherein the interventional instrument is a biopsy needle.

17. The system according to claim 13, where for the calibration measurement a scattering reference sample is used having $\mu_s' d_{fiber}>10$.

18. The system according to claim 13, where for the calibration measurement a reference sample of known phase function and scattering coefficient is used.

19. A computer program product for determining the wavelength dependent absorption coefficient of an actual sample of a turbid medium without prior knowledge of an actual scattering coefficient using overlapping illumination and detection areas, wherein measurements are carried out using a single optical fiber for delivering a light beam towards the actual sample for illumination and for collecting a reflected light beam from the actual sample for detection, wherein a light spot of the delivered light beam used for illumination is overlapping a light spot of the reflected light beam used for detection, the computer program product comprising instructions for causing a processor to carry out the following steps:
a. retrieving a calibration spectrum from a reference measurement using a reference sample;

b. retrieving data of a measurement on the actual sample using the single optical fiber having dimensions between 10 μm and 3 mm to deliver a light towards the actual sample to determine the absolute reflection spectrum using a raw spectrum measured on the actual sample and the calibration spectrum;
c. using the absolute reflection spectrum for determining the wavelength dependent absorption coefficient by minimizing the difference between the measured absolute reflection spectrum and a model function, wherein
d. the model function is modelled using a pre-determined equation based on prior knowledge of the combination of:
  i. a dependence of an effective photon path length on a scattering phase function; and
  ii. a dependence of the absolute reflectance in the absence of absorption on the scattering phase function; and
  iii. an assumed estimate for the scattering coefficient, wherein the effective photon path length and the absolute reflectance in the absence of absorption and are both a function of the assumed estimate for the scattering coefficient, wherein an influence of a mis-estimation of the scattering coefficient on the value of the absolute reflectance in the absence of absorption is at least partially compensated by the influence of the mis-estimation of the scattering coefficient on the value of the effective photon path length such that the wavelength dependent absorption coefficient of the actual sample of the turbid medium is determined without prior knowledge of the actual scattering coefficient.

* * * * *